(12) United States Patent
Pu et al.

(10) Patent No.: US 9,597,530 B2
(45) Date of Patent: Mar. 21, 2017

(54) PARTICLE BEAM SCANNING IRRADIATION SYSTEM

(75) Inventors: Yuehu Pu, Tokyo (JP); Masahiro Ikeda, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 314 days.

(21) Appl. No.: 14/390,087

(22) PCT Filed: May 14, 2012

(86) PCT No.: PCT/JP2012/062278
§ 371 (c)(1),
(2), (4) Date: Oct. 2, 2014

(87) PCT Pub. No.: WO2013/171820
PCT Pub. Date: Nov. 21, 2013

(65) Prior Publication Data
US 2015/0080631 A1    Mar. 19, 2015

(51) Int. Cl.
*G01N 33/48* (2006.01)
*G01N 33/50* (2006.01)
*A61N 5/10* (2006.01)

(52) U.S. Cl.
CPC .......... *A61N 5/1043* (2013.01); *A61N 5/103* (2013.01); *A61N 5/1044* (2013.01); *A61N 2005/1087* (2013.01); *F04C 2270/0421* (2013.01)

(58) Field of Classification Search
None
See application file for complete search history.

(56) References Cited

U.S. PATENT DOCUMENTS

2011/0280372 A1    11/2011   Ivanov

FOREIGN PATENT DOCUMENTS

| JP | 2008-011963 A | 1/2008 |
|---|---|---|
| JP | 2008-099807 A | 5/2008 |
| JP | 2009-66106 A | 4/2009 |
| JP | 2010-279702 A | 12/2010 |
| JP | 2011-156340 A | 8/2011 |
| JP | 2011-177374 A | 9/2011 |
| JP | 2011-212418 A | 10/2011 |

OTHER PUBLICATIONS

The extended European Search Report issued on Mar. 31, 2016, by the European Patent Office in corresponding European Patent Application No. 12876750.6-1666 (7 pgs).
Pardo, J., et al. "Heuristic Optimization of the Scanning Path of Particle Therapy Beams", Medical Physics, vol. 36 Issue 6, pp. 2043-2051, May 5, 2009.
Kang, J., "Dissertation submitted to the Combined Faculties for the Natural Sciences and for Mathematics of the Ruperto-Carola University of Heidelberg, Germany for the degree of Doctor of Natural Sciences", "Optimization of Scanning Parameters in Intensity Modulated Proton Therapy", pp. 1-83, Jul. 21, 2008.
International Search Report (PCT/ISA/210) mailed on *, by the * Patent Office as the International Searching Authority for International Application No. PCT/JP2012/062278.
J. Kang, Optimization of Scanning Parameters in Intensity Modulated Proton Therapy, online, HeiDOK, Jul. 21, 2008, pp. 7-22; internet http://archiv.ub.uni-heidelberg.de/volltextserver/volltexte/2008/8545/.
Inaniwa, et al., "Optimization for fast-scanning irradiation in particle therapy," Medical Physics, Aug. 2007, pp. 3302-3311, vol. 34, No. 8, American Association of Physicists in Medicine.
Kang, et al., "Demonstration of scan path optimization in proton therapy," Med. Phys., Sep. 2007, pp. 3457-3464, vol. 34, No. 9, Am. Assoc. Phys. Med.

*Primary Examiner* — Russell S Negin
(74) *Attorney, Agent, or Firm* — Buchanan Ingersoll & Rooney PC

(57) ABSTRACT

A particle beam scanning irradiation system includes a computer establishing a scanning sequence for irradiation of a tumor portion in a patient; and a particle beam irradiation device irradiating the tumor portion in accordance with the established scanning sequence of the particle beam. The computer selects all conceivable combinations of pairs of irradiation spots among the plurality of irradiation spots arranged in the tumor portion, and determines whether each path for the particle beam to shift between two spots constituting the selected pair passes through the tumor portion; determines a penalty matrix expressing whether each path passes through the tumor portion on the basis of the determination result; evaluates a function for the shift paths on the basis of an optimizing algorithm, and establishes the scanning sequence of the particle beam by an optimized solution of the function.

9 Claims, 7 Drawing Sheets

PARTICLE BEAM SCANNING IRRADIATION SYSTEM

TECHNICAL FIELD

The present invention relates to a particle beam therapy apparatus, more particularly to a particle beam scanning irradiation system for irradiating a diseased portion with a particle beam in accordance with its three-dimensional shape.

BACKGROUND ART

In a particle beam therapy, a diseased portion is irradiated with, for example, a proton beam or a carbon beam accelerated up to 70% of the light velocity. Such a high-energy particle beam has the following characteristics when irradiating into a tumor or the like in a body. Firstly, an irradiating particle beam stops almost at a penetration position proportional to the particle beam energy raised to the 1.7th power. Secondly, the energy density that is imparted to the path through which the irradiating particle beam penetrates until it stops in a body becomes a maximum at the particle beam stop position. The energy density of the particle beam is referred to as a dose. A characteristic depth dose profile formed along the path through which a particle beam penetrates into a body is referred to as "Bragg curve".

The position where the dose of the particle beam becomes a maximum value is referred to as "Bragg peak". The particle beam scanning irradiation system scans a tumor so that the Bragg peak position is kept coincident with its three-dimensional shape. A peak dose at each scanning position is adjusted to form a three-dimensional dose distribution in a target (tumor portion) determined preliminarily by an imaging diagnosis.

A method of scanning irradiation positions with a particle beam includes a scanning method in the lateral directions (X- and Y-directions) substantially orthogonal to the irradiation direction of the particle beam and a scanning method in the depth direction (Z-direction) being the irradiation direction of the particle beam. In the lateral scanning, there are a method of moving a patient with respect to the particle beam and a method of shifting the position of the particle beam using an electromagnet or the like. The latter method using an electromagnet is generally employed.

Varying energy of the particle beam is only method for scanning in the depth direction. Two methods are conceivable for the energy variation: a method of varying the particle beam energy by an accelerator and a method of using an energy varying device called a range shifter installed in a beam delivery line or an irradiation line. Nowadays, the method using an energy varying device is widely employed. A range shifter may sometimes include a device called an energy selection system that performs energy analysis and momentum selection.

The method for lateral scanning of a particle beam is classified into two basic irradiation methods: a spot scanning irradiation method and a hybrid scanning irradiation method. In a spot scanning irradiation method, a particle beam is emitted and intensity of the particle beam is once weakened when an irradiation amount at a given irradiation position reaches a planned value (refer to Non-Patent Document 1). At this time, the particle beam intensity is generally set to zero. To irradiate a next irradiation position with the particle beam, a current value for the scanning electromagnet is changed and the particle beam intensity is increased again, and then the particle beam is emitted. Instead of increasing the particle beam intensity, re-extraction of the particle beam from the accelerator is also made.

In the hybrid scanning irradiation method, while its basic way of irradiating a planned position with the particle beam by a planned amount is the same as with the spot scanning irradiation method, the particle beam is scanned not with its emission being stopped but with the irradiation being continued when shifted to a next irradiation position (refer to Non-Patent Document 2).

PRIOR ART DOCUMENT

Patent Document

Patent Document 1: JP 2011-212418 A
Patent Document 2: JP 2011-156340 A
Patent Document 3: JP 2008-011963 A
Patent Document 4: JP 2008-099807 A
Patent Document 5: JP 2010-279702 A Non-Patent Document Non-Patent Document 1: T. Inaniwa, et al, Medical Physics, 34(8), 2007, pp. 3302-3311
Non-Patent Document 2: J. H. Kang, et al, Medical Physics, 34(9), 2007, pp. 3457-3464

SUMMARY OF THE INVENTION

Problem that the Invention is to Solve

In a particle beam scanning irradiation system described in Non-Patent Document 2, irradiation positions in the same slice are defined as irradiation spots and a scanning sequence for the irradiation spots needs to be preliminarily determined. Moreover, a geometric distance between each pair of the spots is employed as a cost function when the scanning sequence is determined using an optimizing technique.

In the determination of the scanning sequence for the spots in the same slice is, employing the geometric distance between each pair of spots as the cost function brings about a case of causing the particle beam to pass through a vital organ portion that is to be kept from irradiation. In other words, passage of the particle beam through a vital organ portion in shifting between spots does not reflected in the optimization process of the scanning path. The present invention aims at reducing probability that the particle beam passes through a vital organ portion at scanning irradiation.

Means for Solving the Problem

A particle beam scanning irradiation system according to the present invention includes a computer establishing a scanning sequence for irradiation of a tumor portion in a patient with a particle beam; and a particle beam irradiation device irradiating the tumor portion in the patient with the particle beam in accordance with the established scanning sequence of the particle beam, wherein the computer executes a first step of dividing the tumor portion in the patient into a plurality of virtual slices; a second step of determining a positional relationship between the tumor portion sliced in the first step and a healthy organ portion around the tumor portion; a third step of arranging a plurality of spots to be irradiated with the particle beam in the tumor portion sliced in the first step; a fourth step of selecting all conceivable combinations of pairs of irradiation spots among the plurality of irradiation spots arranged in the tumor portion in the third step, and determining whether or not each of shift paths for the particle beam to shift between two irradiation spots constituting the selected pair passes through the tumor portion; a fifth step of determining a penalty matrix having matrix elements expressing whether or not each shift path passes through the tumor portion on the basis of the determination result of the fourth step; and a sixth step of evaluating an evaluation function for the shift paths on the basis of an optimizing algorithm, and establishing the scanning sequence of the particle beam by an optimized solution of the evaluation function obtained from the evaluation.

Advantages of the Invention

A particle beam scanning irradiation system according to the present invention has an effect of reducing an undesired exposure dose imparted to a vital organ portion adjacent to an irradiation range even in a case of scanning irradiation without stopping the beam.

EMBODIMENTS FOR CARRYING OUT THE INVENTION

Embodiment 1

Figure 1:
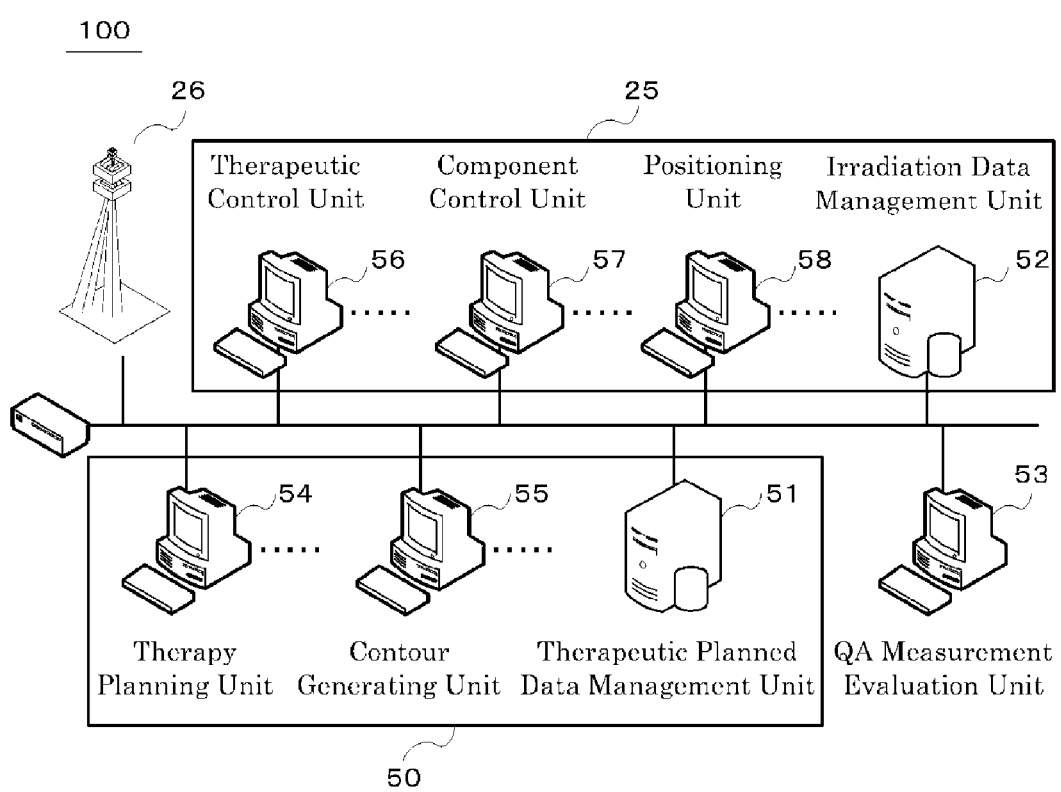
FIG. 1 is a diagram showing an overall configuration of a particle beam scanning irradiation system according to the present invention.

Hereinafter, Embodiments of the present invention will be described with reference to the drawings. FIG. 1 shows an overall configuration of a particle beam scanning irradiation system. The particle beam scanning irradiation system 100 includes a therapeutic particle-beam irradiation control system 25, a particle beam irradiation device 26, a therapy planning system 50, and a QA measurement evaluation unit 53. The therapy planning system 50 is constituted with a therapeutic planned data management unit 51, a therapy planning unit 54, and a contour generating unit 55. The therapeutic particle-beam irradiation control system 25 is constituted with an irradiation data management unit 52, a therapeutic control unit 56, a component control unit 57, and a positioning unit 58.

The therapy planning unit 54 is for creating a therapy plan and simulates a dose calculation on the basis of the therapy plan. The therapeutic control unit 56 controls the particle beam irradiation device 26 to emit the particle beam in accordance with conditions specified by the therapy plan acquired from the irradiation data management unit 52. An actual irradiation dose of the particle beam is measured by the therapeutic control unit 56. The measurement result is transmitted to the therapeutic planned data management unit 51. The therapeutic planned data management unit 51 manages data created by the therapy planning unit 54 and the contour generating unit 55. The irradiation data management unit 52 manages data, therapy records, measurement records, and the like used in the therapeutic control unit 56, the component control unit 57, and the positioning unit 58. The QA measurement evaluation unit 53 compares and evaluates the relation between the measurement result and the therapy plan and the simulation result.

Figure 2:
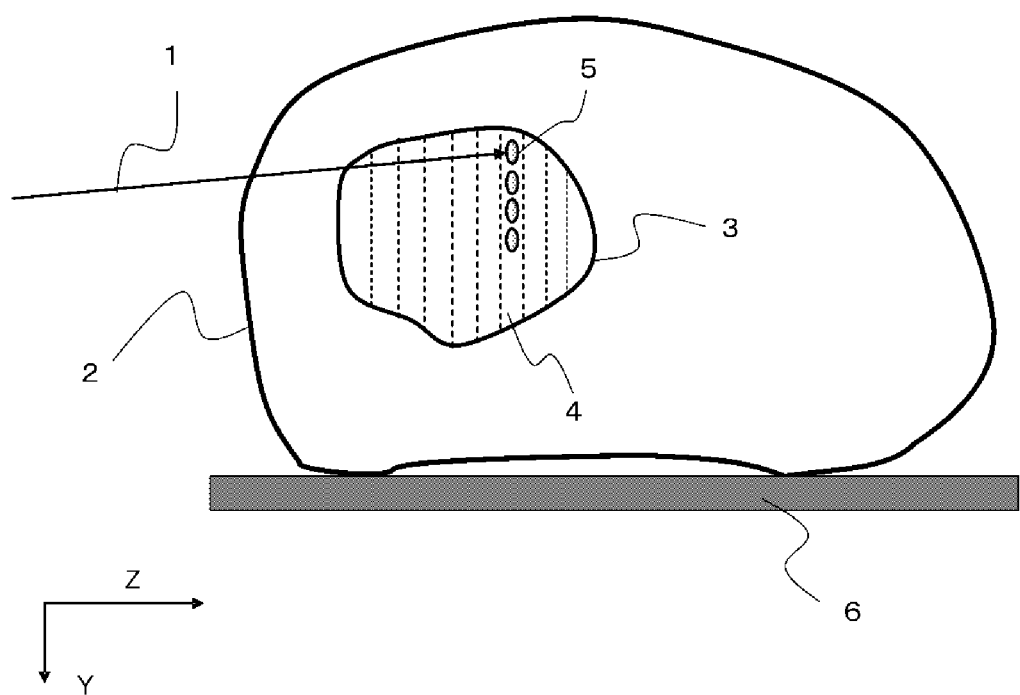
FIG. 2 is a diagram illustrating a sliced state of a diseased portion.

FIG. 2 is a conceptual diagram illustrating the definition of an irradiation slice. A particle beam 1 extracted from the particle beam irradiation device 26 penetrates into a body surface 2 of a patient on a treatment table 6. A tumor portion 3 in the patient body is divided into a plurality of thin virtual irradiation slices 4 in the depthwise direction. In each slice 4, a plurality of irradiation spots 5 are defined as being arranged two-dimensionally. The irradiation slice means a positional grouping of spots irradiated with the particle beam having the same energy.

Figure 3:
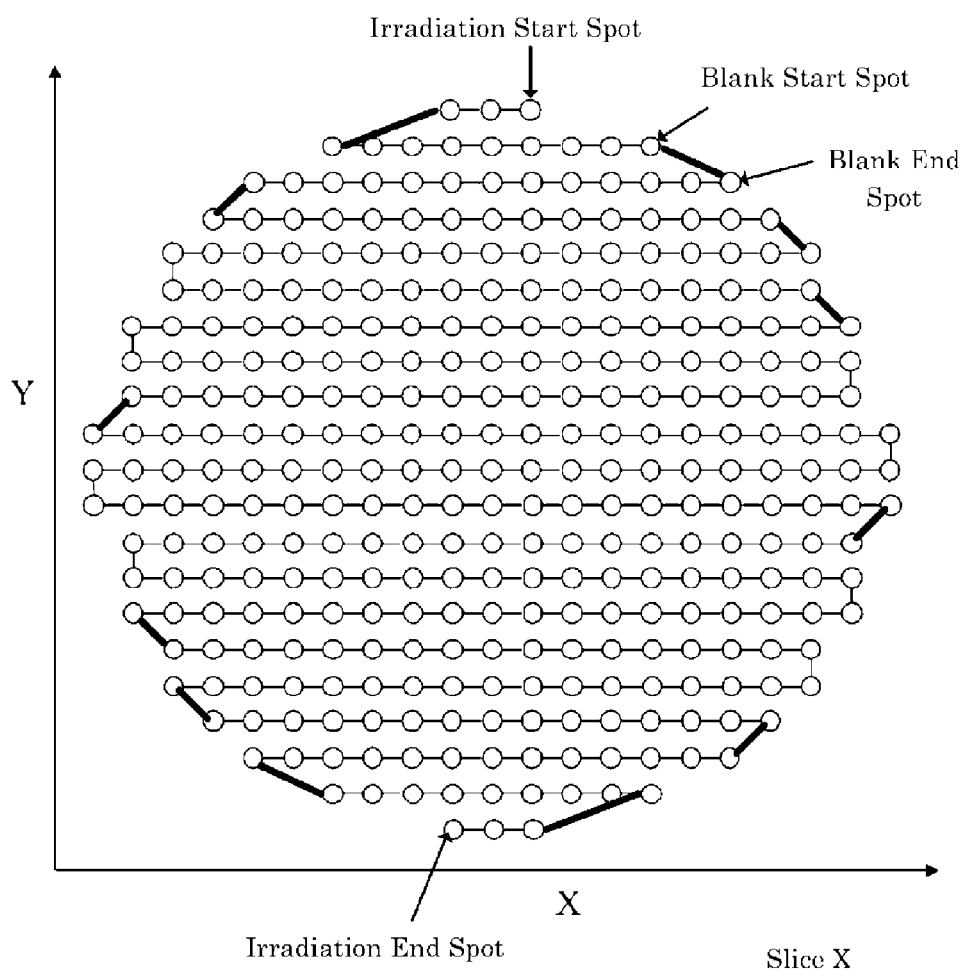
FIG. 3 is a diagram illustrating a positional relationship between an irradiation start spot and an irradiation end spot.

Next, a basic scanning sequence of the particle beam in a scanning irradiation is described with reference to FIG. 3. An arrangement of irradiation spots and a scanning path of the particle beam in a given irradiation slice X are illustrated in the figure. The particle beam moves along the path in a single stroke writing manner in principle from a start spot of the irradiation to an end spot of the irradiation. The particle beam ordinarily moves with a scan shift to an adjoining irradiation spot. When irradiation spots are distant, the particle beam moves with a blank shift to a next irradiation spot to skip between the irradiation spots. The number of spots that are omitted from the irradiation by the blank shift is different depends on irradiation conditions. The blank shift is started from a blank start spot and ended at a blank end spot.

Figure 4:
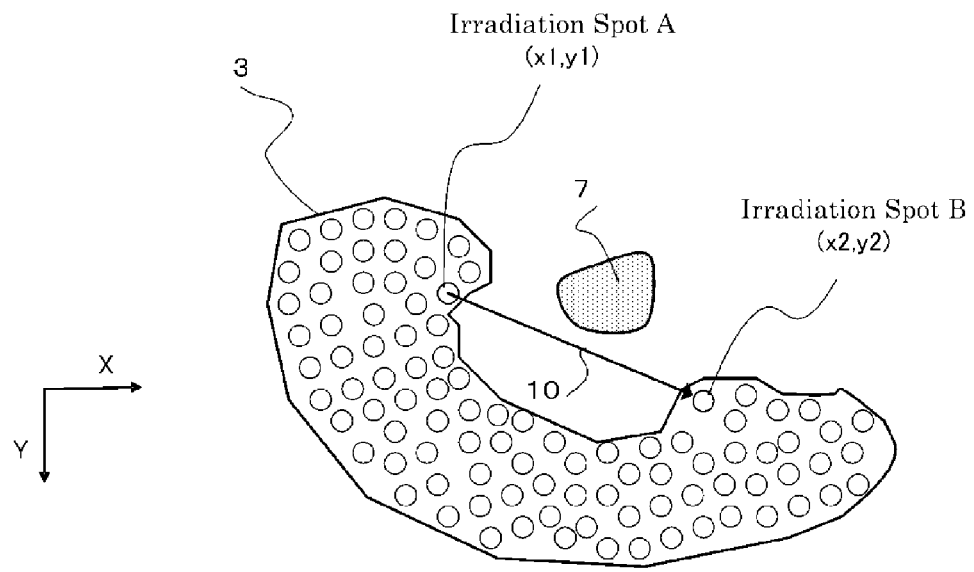
FIG. 4 is a conceptual diagram illustrating a relationship between a tumor portion and a vital organ portion in an irradiation slice.

FIG. 4 is a conceptual diagram illustrating a relationship between a tumor portion and a vital organ portion in an irradiation layer. Positional coordinates $(x_i, y_i)$ are assigned to all irradiation spots. An irradiation spot A and an irradiation spot B arranged in the tumor portion 3 have respective positional coordinates $(x_1, y_1)$ and $(x_2, y_2)$. A geometric straight line 10 is the shortest line connecting between the irradiation spot A and the irradiation spot B. In FIG. 4, the geometric straight line 10 does not pass through the vital organ portion 7.

Figure 5:
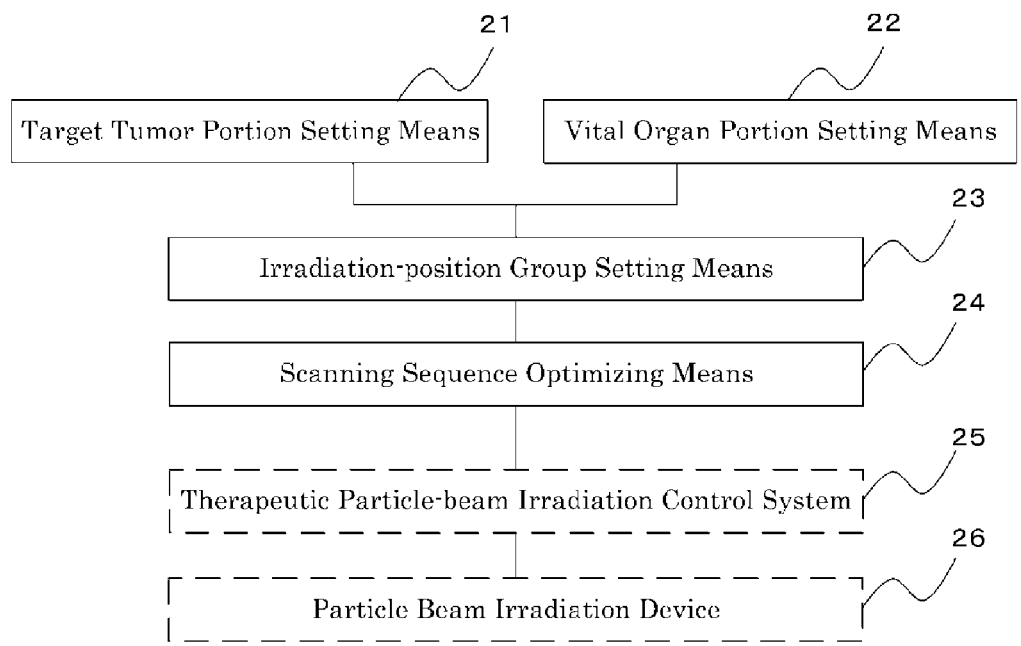
FIG. 5 is a block diagram showing a configuration example of the particle beam scanning irradiation system according to an embodiment of the present invention.

The scanning sequence of the particle beam is preliminarily calculated by the therapy planning system 50. FIG. 5 is a block diagram showing a software configuration of the therapy planning system 50 according to the present invention. The therapy planning system 50 is constituted with a target tumor portion setting means 21, a vital organ portion setting means 22, an irradiation-position group setting means 23, a scanning sequence optimizing means 24, and others. The target tumor portion setting means 21 sets an irradiation range of the particle beam as a target tumor portion. The vital organ portion setting means 22 sets as a vital organ portion a healthy organ portion that needs to be kept from irradiation exposure as much as possible. The irradiation-position group setting means 23 divides a volumetric target tumor portion into irradiation layers to set a positional grouping in each irradiation layer. The scanning sequence optimizing means 24 determines a scanning sequence for each irradiation position in each irradiation layer. The therapy planning unit 54 corresponds to the irradiation-position group setting means 23 and the scanning sequence optimizing means 24. The contour generating unit 55 corresponds to the target tumor portion setting means 21 and the vital organ portion setting means 22.

An operation of the particle beam scanning irradiation system according to the present invention is described next with reference to FIG. 6. First, on the basis of computer tomography (CT) data and the like of a patient, patient-body contour information and three-dimensional diseased portion information are extracted using the therapy planning system 50, whereby contours of a body surface 2 and a tumor portion 3 are determined (ST2). The target tumor portion setting means 21 sets an irradiation range of the particle beam as a volumetric target tumor portion. At the same time, a vital organ portion to be kept from irradiation exposure is set using the vital organ portion setting means 22.

Next, the volumetric target tumor portion is divided into irradiation layers. In each irradiation layer, irradiation slices are set in the three-dimensional target tumor portion using the irradiation-position group setting means 23 (ST3). In each irradiation slice, a positional grouping of irradiation spots is set (ST4). The particle beam 1, which penetrates into the body surface 2, has substantially the same beam energy when used for the irradiation spots in the same irradiation slice. When a different irradiation slice is irradiated, the beam energy of the particle beam 1 is altered.

The scanning sequence for the irradiation spots in each irradiation layer is determined by the scanning sequence optimizing means 24. While the particle beam generally shifts along a curved line, Embodiment 1 deals with a case of a straight-line shift of the particle beam. In order to determine a scanning sequence that skirts a vital organ portion, a geometric straight-line distance $L_{ij}$ between an arbitrary pair of irradiation spots is calculated first for all irradiation spots included in an irradiation slice to make allowance for a scanning path optimizing operation. The geometric straight-line distance $L_{ij}$ is represented as SQRT{$(x_i-x_j)*(x_i-x_j)+(y_i-y_j)*(y_i-y_j)$}, where the symbols i and j indicate location numbers of the two irradiation spots.

Furthermore, a penalty matrix $P_{ij}$ having elements $C_1$ and $C_2$ is calculated for the arbitrary pair of irradiation spots (ST5). The element $C_1$ is assigned when the geometric straight line 10 from a spot position (i) to a spot position (j) passes through the vital organ portion 7. The element $C_0$ is assigned when the geometric straight line 10 from a spot position (i) to a spot position (j) does not pass through the vital organ portion 7. Note that the element $C_1$ is larger than the element $C_0$, and the element $C_0$ is set to be one and the element $C_1$ is set to be zero in Embodiment 1 for the sake of explanatory convenience. When a geometric straight line connecting between a pair of irradiation spots passes through the vital organ portion, a larger penalty can be imposed by adjusting the elements $C_1$ and $C_0$.

The scanning sequence for the irradiation spots in an irradiation slice can be determined by optimizing a cost function CF, which is an evaluation function, so that the function becomes a minimum. The cost function is constituted as below with an evaluation parameter (the geometric straight-line distance $L_{ij}$) and the penalty matrix $P_{ij}$ for each shift path. A weight addition method ($CF_1$) and a weight multiplication method ($CF_2$) are conceivable for a method for obtaining from the geometric straight-line distance $L_{ij}$ an evaluation factor weighted using the penalty matrix $P_{ij}$.

$$CF_1 = \Sigma_{ij}(L_{ij} + a \times P_{ij})$$

$$CF_2 = \Sigma_{ij}(L_{ij} \times W_{ij})$$

$$W_{ij} = 1 \text{ (if } P_{ij} = 0)$$

$$W_{ij} = a \text{ (if } P_{ij} = 1),$$

where an adjustment factor "a" serves an adjusting function for skirting a vital organ portion. A larger adjustment factor "a" makes it less likely to select a path passing through the vital organ portion.

The cost function calculates a numerical summation of the evaluation factors for all pairs of irradiation spots included in the same irradiation slice. As a specific optimizing algorithm, it is common to use a fast simulated annealing method described in Non-Patent Document 2. Employing another optimizing algorithm, for example, a genetic algorithm, if used along with the cost function according to this embodiment, can also bring about a similar effect. As a result of the optimizing calculation, an irradiation sequence that skirts the vital organ portion 7 is preferentially obtained.

Figure 6:
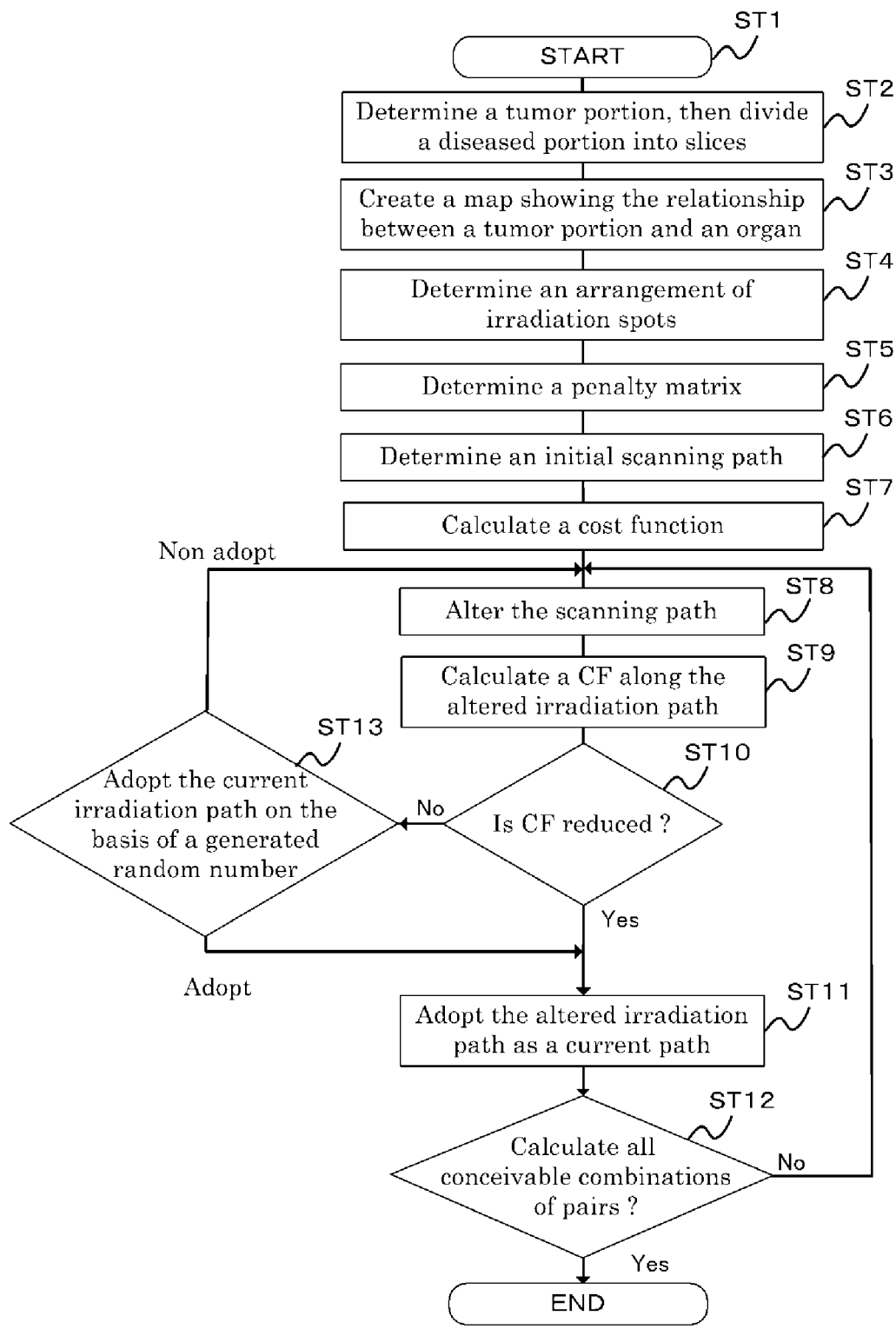
FIG. 6 is a flowchart showing a procedure of determining an optimized solution according to the embodiment of the present invention.

The flowchart in FIG. 6 shows a specific procedure when the fast simulated annealing method is employed in this embodiment. After the penalty matrix is determined, an initial scanning sequence is generated (ST6). The initial scanning sequence is set as a scanning sequence that simply connects all irradiation spots by a line of single stroke writing. A cost function is calculated for the initial scanning sequence, and a current cost function $CF_0$ is obtained (ST7). Next, two arbitrary irradiation spots are selected among the irradiation spots in the irradiation slice on the basis of a generated random number, and a new scanning sequence is generated by regarding these two spots as anchor points (ST8). A cost function CF is calculated for the new scanning sequence candidate to obtain a new $CF_1$ (ST9). The new $CF_1$ is compared with the current $CF_0$ (ST10). If the new $CF_1$ is smaller than the current $CF_0$, the new scanning sequence is adopted and the new $CF_1$ is set as a temporary current $CF_z$ (ST11).

If the new $CF_1$ is larger than the current $CF_0$ as a result of the comparison, the new scanning sequence is adopted with a certain probability (ST13). A criterion for the probability to be employed is calculated from the adjustment factor, an assumed probability distribution, and the difference between the new $CF_1$ and the current $CF_0$ in the fast simulated annealing method. According to the optimizing algorithm, a scanning sequence that makes shortest a total length of the scanning path and skirts the vital organ portion is preferentially obtained as an optimized solution (ST12).

Consequently, a scanning sequence for irradiation that skirts a vital organ that needs reduction of undesired exposure can be obtained in the particle beam scanning irradiation, thus realizing an accurate particle-beam irradiation system. The optimized scanning sequence obtained for each irradiation slice and positional coordinates $(x_i, y_i)$ of each irradiation spot are transmitted to the therapeutic particle-beam irradiation control system 25. The particle beam irradiation device 26 constituted with a scanning electromagnet, a scanning power supply, a beam monitor, and the like is actually controlled to irradiate each slice in the tumor portion 3 with a particle beam in accordance with a therapy plan.

Thus, according to a particle beam scanning irradiation system described in Embodiment 1 of the present invention, an irradiation scanning sequence can be obtained that skirts as much as possible a vital organ that needs reduction of undesired exposure in a scanning irradiation using a particle beam, thereby realizing a particle beam irradiation system of high accuracy.

Embodiment 2

Figure 7:
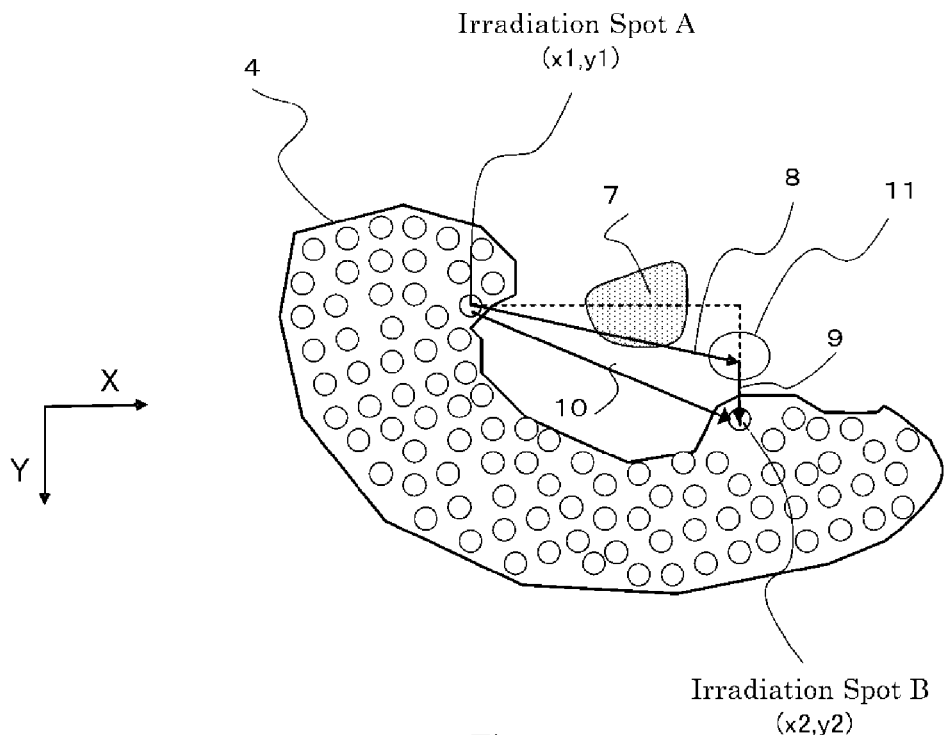
FIG. 7 is a diagram illustrating a relationship between a segmented scanning path and a geometric straight line, according to an embodiment of the present invention.

In calculating a penalty matrix $P_{ij}$ in Embodiment 1, whether or not the particle beam passes through a vital organ portion 7 is determined according to whether a geometric straight line 10 connecting between a spot position (i) and a spot position (j) passes through the vital organ portion 7. In an actual particle beam scanning irradiation system, deflection velocities of the scanning electromagnet are in many cases different in the X-direction and Y-direction. In a case of the X-direction deflection velocity being faster than the Y-direction deflection velocity, when the particle beam is controlled to shift from an irradiation spot A to an irradiation spot B, the particle beam actually shifts first from the irradiation spot A to a spot-shift middle position 11 and then shifts from the spot-shift middle position 11 to the irradiation spot B, as illustrated in FIG. 7. In the scanning irradiation, a partial particle-beam path 8 is the former half of the path when the particle beam is scanned from the irradiation spot A to the irradiation spot B, and a partial particle-beam path 9 is the latter half of the path when the particle beam is scanned from the irradiation spot A to the irradiation spot B.

Even in such the case, when the particle beam is shifted between irradiation spots, it is possible to render straight the particle-beam shift path connecting between the irradiation spots by controlling the power supply for the scanning electromagnet X responsible for X-direction positions and the scanning electromagnet Y responsible for Y-direction positions. In this case, however, control of the scanning power supply presumably become complicated.

When the particle beam shifts between irradiation spots, if the scanning electromagnets for the X-direction and the Y-direction scans the particle beam with respective maximum scanning velocities, the scanning control can be performed simply. On this occasion, an actual shift path of the particle beam is along the partial particle-beam path 8 and the partial particle-beam path 9. In this case, the partial particle-beam path 8 or the partial particle-beam path 9 passes through the vital organ portion 7, while the geometric straight line 10 connecting between the irradiation spots A and B does not pass through the vital organ portion 7.

In calculating the penalty matrix $P_{ij}$ in Embodiment 2, determination whether or not the particle beam passes through the vital organ portion 7 is made on the basis not of the geometric straight line 10 connecting between a spot position (i) and a spot position (j), but of whether the partial particle-beam paths 8 and/or 9 along which the particle beam actually shifts pass through the vital organ portion 7 when the scanning electromagnets X and Y scan the particle beam with respective maximum scanning velocities. When an irradiation spot indicated by positional coordinates ($X_1$, $Y_1$) shifts with an X-direction scanning velocity $V_x$ and a Y-direction scanning velocity $V_y$, the positional coordinates (X(t), Y(t)) of the irradiation spot after a time t elapses are calculated by the following equations:

$$X(t) = X_1 + V_x \times t, \text{ and}$$

$$Y(t) = Y_1 + V_y \times t.$$

Determination whether or not the particle beam passes through the vital organ portion 7 is made on the basis of a curve following a path calculated by the above equations.

When a path between a pair of irradiation spots is determined to pass through a vital organ portion, a larger penalty is imposed to the distance between the irradiation spot pair by assigning a larger value to the element $C_1$ of the penalty matrix $P_{ij}$. Otherwise, a larger adjustment factor "a" may be assigned to the penalty matrix $P_{ij}$. According to Embodiment 2, with a simpler scanning control, a faster scanning irradiation can be performed and a vital organ portion can be surely kept form the irradiation as well. This realizes a particle beam scanning irradiation system of higher accuracy.

Embodiment 3

In Embodiments 1 and 2, only the center locus of a particle beam shift is discussed for the determination whether or not the particle beam passes through a vital organ portion 7 in calculating the penalty matrix $P_{ij}$. In the actual irradiation, the irradiation spot has a finite size. Taking into account the spot size as well as the above-described shift path between spots at the same time in calculating the penalty matrix $P_{ij}$, accuracy of the scanning irradiation is enhanced.

Determination whether or not the particle beam, when shifting from the irradiation spot position A to the irradiation spot position B, for example, shifting along the partial particle-beam path 8 shown in FIG. 7, passes through the vital organ portion 7, may be made taking the actual size and shape of the particle beam into account. This makes it possible, in scanning the particle beam with high accuracy, to obtain such an optimum scanning sequence that keeps a vital organ portion from the particle beam region, even when the particle beam has a large spot size. Consequently, a particle beam scanning irradiation system of higher accuracy can be realized.

Embodiment 4

In Embodiment 4, a total scan time $T_{ij}$ is used as a target to be optimized for calculating a cost function. That is, the cost function is calculated using the total scan time $T_{ij}$ instead of the geometric straight-line distance $L_{ij}$. The scan time from a spot position (i) to a spot position (j) can be calculated from the following equation using the X-direction scanning velocity $V_x$ and the Y-direction scanning velocity $V_y$:

$$T_{ij} = \max(\text{abs}(x_j - x_i)/V_x, \text{abs}(y_j - y_i)/V_y),$$

where "abs(A)" represents the absolute value of "A" and "max(A, B)" represents larger one of "A" and "B".

For the sake of convenience in postulation of a case with raster scanning, the X-direction scanning velocity $V_x$ and the Y-direction scanning velocity $V_y$ are assumed constant in the above equation. However, the total scanning time $T_{ij}$ may be calculated taking into account such acceleration and deceleration as "stop state"→"accelerating"→"constant velocity state"→"decelerating"→"stop state", as is the case with the hybrid scanning.

Embodiment 5

Figure 8:
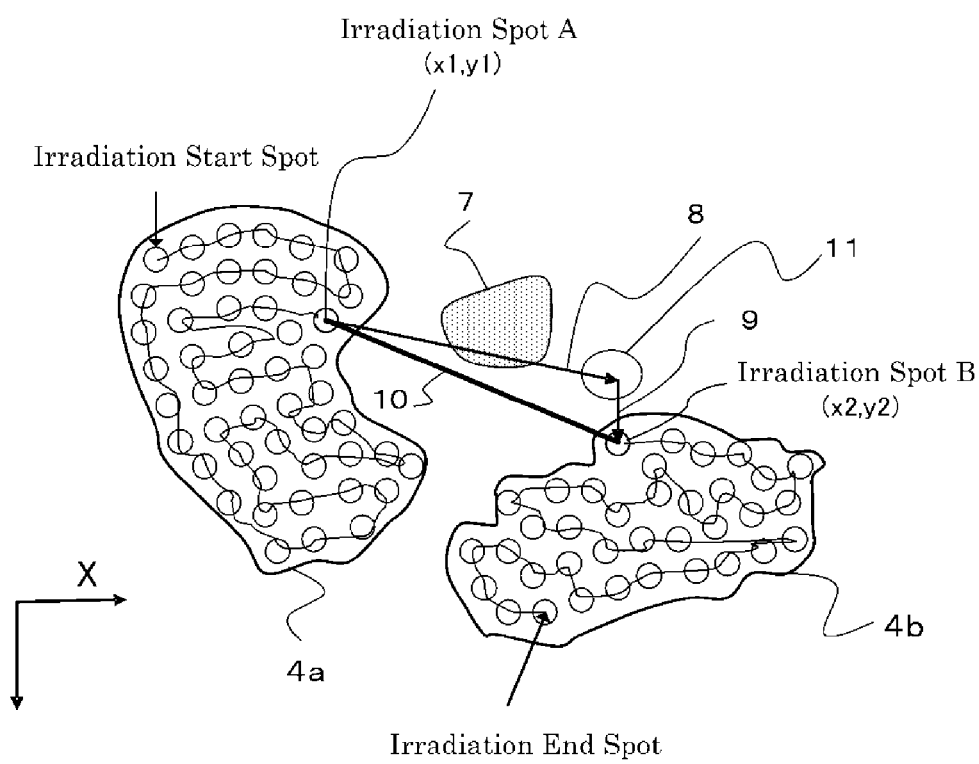
FIG. 8 is an example diagram illustrating an automatic slice segmentation process according to Embodiment 5 of the present invention.
Figure 9:
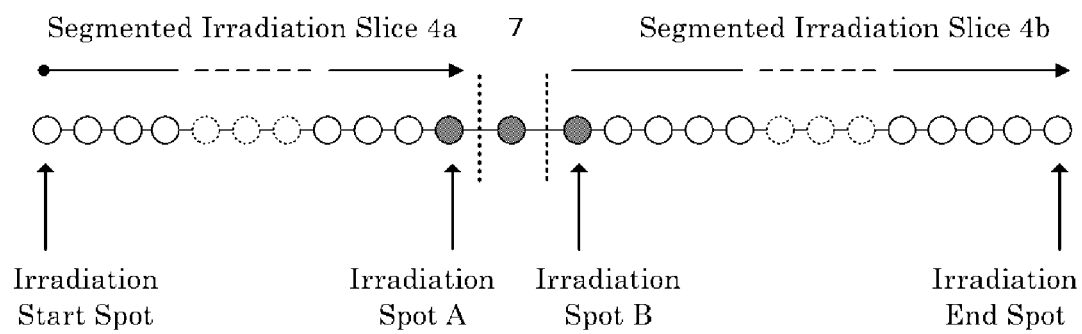
FIG. 9 is a diagram for explaining additionally the automatic slice segmentation process.

Next, an operation of the particle beam scanning irradiation system is described according to Embodiment 5 of the present invention with reference to FIGS. 8 and 9. FIG. 8 illustrates an example of an automatic slice segmentation process. A segmented irradiation slice 4a and a segmented irradiation slice 4b represent the former half portion and the latter half portion of the irradiation slice 4, respectively. As shown in FIG. 9, the irradiation of the segmented irradiation slice 4a starts at an irradiation start spot and ends at an irradiation spot A. Likewise, the irradiation of the segmented irradiation slice 4b starts at an irradiation start spot B and ends at an irradiation spot. A vital organ portion 7 exists between the irradiation spot A and the irradiation start spot B.

The operation according to Embodiment 5, of the particle beam scanning irradiation system is basically the same as those in the above embodiments. It is assumed that such a single-stroke-writing scanning sequence that starts at the irradiation start spot and ends at the irradiation end spot as shown in FIG. 9 is obtained as a result of optimizing, by means of the scanning sequence optimizing means 24, a scanning sequence for each irradiation spot in each irradiation layer described in Embodiment 1 in the particle beam scanning irradiation system. Because the optimizing technique (fast simulated annealing method) is a probabilistic technique, such a scanning sequence that a scanning path connecting between the irradiation spot A and the irradiation spot B involves the vital organ portion 7 may be in some cases obtained depending on a value of the adjustment factor "a".

On this occasion, the scanning sequence optimizing means 24 automatically segments the irradiation slice 4 into two: the segmented irradiation slice 4a and the segmented irradiation slice 4b at the scanning path regarded as a segmentation boundary, where the shift passes through the vital organ portion 7 from the irradiation spot A to the irradiation start spot B. After that individual scanning sequences are generated for the segmented irradiation slices 4a and 4b. The segmented irradiation slices 4a and 4b are redefined as two separate irradiation slices.

This segmentation process can eliminate perfectly a path that passes through the vital organ portion 7. The segmented irradiation slices 4a and 4b are regarded as separate slices and their spot position information and respective scanning sequences are transmitted to the therapeutic particle-beam irradiation control system 25. The irradiation is performed lastly by the particle beam irradiation device 26. Consequently, the particle beam scanning irradiation system according to Embodiment 5 demonstrates the effect of irradiating with higher accuracy a diseased portion with the particle beam. This method can be similarly applied to a case with three or more pairs of irradiation spots connected by scanning paths that pass through a vital organ portion 7.

In the present invention, each embodiment may be freely combined and/or appropriately modified and/or omitted within the scope and spirit of the invention.

REFERENCE NUMERALS

1: particle beam, 2: body surface, 3: tumor portion, 4: irradiation slice, 5: irradiation spot, 6: treatment table, 7: vital organ portion, 8: partial particle-beam scanning path, 9: partial particle-beam scanning path, 10: geometric straight line, 11: spot-shift middle position, 21: target tumor portion setting mean, 22: vital organ portion setting means, 23: irradiation-position group setting means, 24: scanning sequence optimizing means, 25: therapeutic particle-beam irradiation control system, 26: particle beam irradiation device, 4a: segmented irradiation slice, 4b: segmented irradiation slice, 50: therapy planning system, 51: therapeutic planned data management unit, 52: irradiation data management unit, 53: QA measurement evaluation unit, 54: therapy planning unit, 55: contour generating unit, 56: therapeutic control unit, 57: component control unit, 58: positioning unit, 100: particle beam scanning irradiation system.

The invention claimed is:

1. A particle beam scanning irradiation system comprising:

a computer establishing a scanning sequence for irradiation of a tumor portion in a patient with a particle beam; and a particle beam irradiation device irradiating the tumor portion in the patient with the particle beam in accordance with the established scanning sequence of the particle beam, wherein the computer executes a first step of dividing the tumor portion in the patient into a plurality of virtual slices;

a second step of determining a positional relationship between the tumor portion sliced in the first step and a healthy organ portion around the tumor portion;

a third step of arranging a plurality of spots to be irradiated with the particle beam in the tumor portion sliced in the first step;

a fourth step of selecting all conceivable combinations of pairs of irradiation spots among the plurality of irradiation spots arranged in the tumor portion in the third step, and determining whether or not each of shift paths for the particle beam to shift between two irradiation spots constituting the selected pair passes through the tumor portion;

a fifth step of determining a penalty matrix having matrix elements expressing whether or not each shift path passes through the tumor portion on the basis of the determination result of the fourth step; and a sixth step of evaluating an evaluation function for the shift paths on the basis of an optimizing algorithm, and establishing the scanning sequence of the particle beam by an optimized solution of the evaluation function obtained from the evaluation, wherein the evaluation function is a total summation of evaluation factors each including an evaluation parameter for each shift path and an element of the penalty matrix therefor.

2. The particle beam scanning irradiation system of claim 1, wherein the evaluation parameter for each shift path represents a length of a geometric straight line connecting two irradiation spots constituting a pair.

3. The particle beam scanning irradiation system of claim 2, wherein a matrix element of the penalty matrix is assigned a certain reference value when determination is made in the fourth step that a shift path of the particle beam does not pass through the tumor portion, and is assigned a value larger than the reference value when determination is made in the fourth step that a shift path of the particle beam passes through the tumor portion.

4. The particle beam scanning irradiation system of claim 1, wherein the evaluation parameter for each shift path represents a time required for the particle beam to shift between two irradiation spots constituting a pair.

5. The particle beam scanning irradiation system of claim 1, wherein a geometric straight line connecting two irradiation spots constituting a pair is used for a shift path of the particle beam when determination is made in the fourth step whether or not the shift path of the particle beam passes through the tumor portion.

6. The particle beam scanning irradiation system of claim 1, wherein an actual shift path of the particle beam is used for a particle-beam shift path when determination is made in the fourth step whether or not the particle-beam shift path passes through the tumor portion.

7. The particle beam scanning irradiation system of claim 1, wherein a shift path of the particle beam is regarded to have a width the same as a size of the irradiation spot when determination is made in the fourth step whether or not the shift path of the particle beam passes through the tumor portion.

8. The particle beam scanning irradiation system of claim 1, wherein when determination is made in the fourth step that a shift path of the particle beam between two irradiation spots constituting a pair passes through the tumor portion in a slice, the computer further executes a seventh step of segmenting the slice at the shift path regarded as a segmentation point, and redefining the slice as two segmented slices.

9. The particle beam scanning irradiation system of claim 1, wherein the total summation of evaluation factors is performed for all the conceivable combinations of pairs of irradiation spots.

* * * * *